United States Patent
Koenig et al.

(10) Patent No.: US 6,945,962 B2
(45) Date of Patent: Sep. 20, 2005

(54) SEQUENTIAL SYRINGE APPARATUS

(76) Inventors: Edward L. Koenig, 33 Stone Fence Rd., Bernardsville, NJ (US) 07924; Ronald C. DeSimoni, 21 Round Hill Rd., Kinnelon, NJ (US) 07405; Martin T. Mortimer, deceased, late of Telford, PA (US); by Jeffrey S. Mortimer, legal representative, 918 S. 16th St., Arlington, VA (US) 22202

( * ) Notice: Subject to any disclaimer, the term of this patent is extended or adjusted under 35 U.S.C. 154(b) by 0 days.

(21) Appl. No.: 10/176,030

(22) Filed: Jun. 21, 2002

(65) Prior Publication Data

US 2003/0236503 A1 Dec. 25, 2003

(51) Int. Cl.$^7$ .......................... A61M 5/00; A61M 5/24
(52) U.S. Cl. ................ 604/208; 604/191; 604/203
(58) Field of Search ................ 604/186, 191, 604/200, 201, 207, 244, 208–211

(56) References Cited

U.S. PATENT DOCUMENTS

| | | | | |
|---|---|---|---|---|
| 2,764,981 A | * | 10/1956 | Helmer et al. | 604/210 |
| 2,869,541 A | * | 1/1959 | Helmer et al. | 604/210 |
| 3,911,916 A | * | 10/1975 | Stevens | 604/191 |
| 3,934,586 A | * | 1/1976 | Easton et al. | 604/208 |
| 4,055,177 A | * | 10/1977 | Cohen | 604/88 |
| 4,702,737 A | * | 10/1987 | Pizzino | 604/191 |
| 4,790,822 A | * | 12/1988 | Haining | 604/110 |
| 5,429,610 A | * | 7/1995 | Vaillancourt | 604/191 |
| 2003/0105433 A1 | * | 6/2003 | Ruben | 604/191 |

* cited by examiner

*Primary Examiner*—Michael J. Hayes
(74) *Attorney, Agent, or Firm*—Bernard Malina; Malina & Associates, PC

(57) ABSTRACT

A medical sequential syringe apparatus has two or more fluids of predetermined volume dispensed therefrom. The apparatus includes a tubular cartridge containing fluid is sealed at one end by a membrane with a hollow tubular spike mounted at one end of the body facing inwardly into the tubular body. A plunger mounted within the tubular body moves the cartridge toward the spike to puncture the membrane and allow the fluid to flow from the cartridge through the hollow of the spike out of the tubular body.

3 Claims, 2 Drawing Sheets

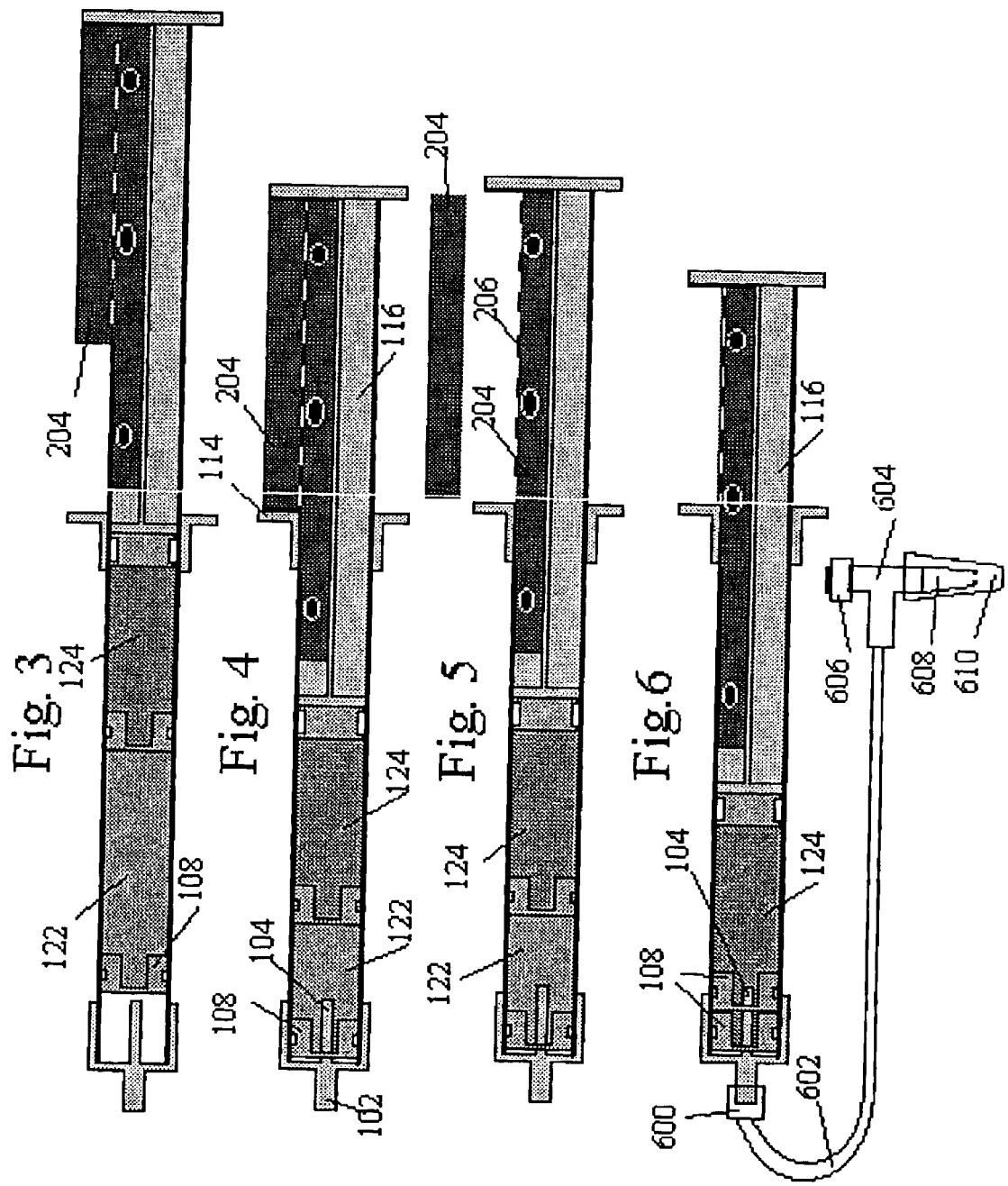

SEQUENTIAL SYRINGE APPARATUS

FIELD OF THE INVENTION

This invention relates to a syringe and more particularly, to a medical sequential syringe apparatus having two or more fluids of predetermined volume dispensed from a compartmentalized syringe in a manner that does not mix the fluids.

A typical application of the present invention is the placing of fluid for sealing purposes which would be followed immediately by a hardener to cause rapid curing. Another application might be medical procedures where one administered fluid medication is applied and is usually followed by another fluid. The present invention may be used in the construction trades, manufacturing as well as the medical fields.

The invention provides for positively stopping the application once or multiple times in order to facilitate other user operations. Such stoppages would be instituted after a predetermined volume of fluid(s) was dispensed. This feature is useful in the administration of repeated small volumes of alternating fluids to facilitate testing of remotely located chemistry such as determining field chemistry during the growing season.

The use of the invention as an infusion device is further facilitated by the ability of the caregiver to insure patient fluid transfer by traditional draw back of the syringe plunger.

BACKGROUND OF THE INVENTION

Mixing syringes are presently used in industrial and medical applications. They are used to mix epoxies just prior to application as well as various other product fluids. There is, however, a need for a device that does not mix fluids but allows that the fluids be maintained in an ordered sequential manner for their use to be effective and safe.

Currently available syringe apparatus are disadvantageous in that they require multiple syringes or other devices that each require packaging, may be separated from each other in storage facilities, are difficult to track during long term procedures, and are generally cumbersome to use.

Medicinal fluids, for example, are best maintained in storage as part of a particular process which requires all portions be in specific volumes. Currently, in some cases, these volumes are measured from bulk storage just prior to use and for best results, separate syringes are used to apply them in sequence which requires further handling by the medical technician or nurse.

Additionally, there may be a need to intervene between the application of subsequent fluids after the first is applied. This intervention may be for a brief moment or a considerable time, during which the operator may become confused as to just what step in the process is next to be done. The present invention is particularly useful for such activity and alerts the operator as to the next successive step without the need of undue paraphernalia. This makes the process simpler and more certain of being properly executed sequentially and with the desired result. Examples of prior art devices are shown in U.S. Pat. No. 4,185,628 (Kopfer); U.S. Pat. No. 4,029,236 (Carson); U.S. Pat. No. 5,310,091 (Dunning); U.S. Pat. No. 5,020,694 (Pettengill); U.S. Pat. No. 5,032,117 (Motta); U.S. Pat. No. 5,429,603 (Morris); U.S. Pat. No. 5,000,736 (Kaufhold); U.S. Pat. No. 5,222,948 (Austin); U.S. Pat. No. 4,405,317 (Case); U.S. Pat. No. 4,412,836 (Brignola); U.S. Pat. No. 4,412,836 (Brignola); U.S. Pat. No. 4,865,587 (Walling); and U.S. Pat. No. 5,004,460 (Gimeno).

SUMMARY OF THE INVENTION

The present invention provides a prefilled syringe with two or more segregated volumes of different fluids. As the plunger of the syringe is depressed, the most distal volume of fluid moves a puncture diaphragm towards a slotted spike located inside the end cap of the syringe and facing towards the puncture diaphragm.

The slotted spike is hollow and leads fluids to the opening at the distal end of the syringe once it punctures the diaphragm that is impaled upon the spike. This process is repeated each time a puncture diaphragm is pressed onto the hollow slotted spike as the plunger of the syringe is depressed further into the syringe by the user.

The capability exists to install numerous flags as a means to stop forward motion of the syringe plunger at predetermined positions of the plunger's forward travel. These positions relate to specific volumes of the fluids that have been preloaded and are being dispensed by the device. One such stop may be utilized to precisely fill the syringe, and/or any attached appendages required for the particular application, with the first fluid.

The device may be a disposable unit or a unit that operates by means of a replaceable cartridge containing the fluids necessary for a particular application in which case the unit would be considered reusable.

Depending on the application to which the device is assigned, the assembly of the fluids and the associated containers, syringe, etc. would be accomplished in suitable facilities and under the guidance of appropriate protocols. Packaging requirements would be less than those required for individual items used in current practice. In addition, the cost of manufacture is reduced.

BRIEF DESCRIPTION OF THE DRAWINGS

FIG. 3 is a partially schematic view of the preferred embodiment of FIG. 1 in the condition just prior to use;

FIG. 4 is a partially schematic view of the preferred embodiment of FIG. 1 in the condition where an intentional stop has been encountered;

FIG. 5 is a partially schematic view of the preferred embodiment of FIG. 1 illustrating the removal of the intentional stop;

FIG. 6 is a partially schematic view of the preferred embodiment of FIG. 1 illustrating continued plunger movement after the above stop is removed and showing an attached catheter extension such as would be utilized in a medical application.

DETAILED DESCRIPTION OF THE INVENTION

Figure 1:
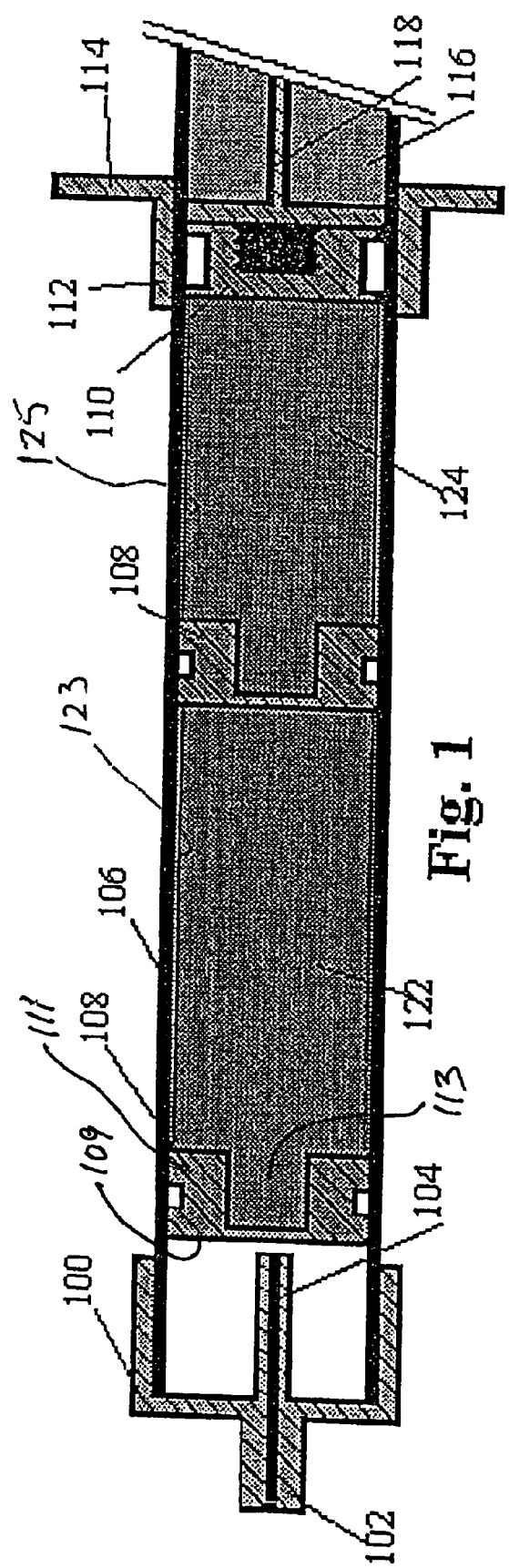
FIG. 1 is a partially schematic cross section view of a preferred embodiment of the present invention including the distal portion of the plunger.

Referring to FIG. 1, the device is primarily cylindrical in shape, the cross section being through the axis of the cylinder. The device 10 comprises a cylinder defined as the syringe body (106) with fittings or caps at each end. The distal end cap (100) presents an end cap termination (102) which is determined by the application. In a medical version of the invention, this may, for example, be a male luer lock. Internal to the assembled device 10 is the end cap slotted spike (104) which is hollow and allows the fluids (122, 124) in tubular cartridges (123, 125) to be passed through to the end cap termination (102). The end cap slotted spike is placed as shown to pierce the puncture diaphragms (108) through a central membrane area (109) when the spike is forced to move to the left (in the drawings) by the action of the plunger tip (110) being pushed into the syringe body (106) by the plunger (116). The central membrane area (109) is of thinner cross-section than adjacent area (111) of the diaphragm (108) and forms therein a U-shaped recess (113).

The liquids (122,124) prefilled between the puncture diaphragms (108) and the plunger tip (110) transmit the forces from the plunger (116) to the puncture diaphragms causing the puncture diaphragms to be impaled upon the end cap slotted spike(104). The slotted spike (104) allows the puncture diaphragms (108) to be pushed to the base of the slotted spike (104) by permitting egress of any liquids between the distal end cap (100) and the puncture diaphragms (108).

FIG. 1 shows the proximal end cap (112) and the portion of it that represents the finger grips (114). The user would generally place the first and second fingers of their hand upon the distal surface of these finger grips to enable the plunger distal plate (202) (FIG. 2) to be effectively depressed by the thumb of the same hand as is done with a normal syringe.

Figure 2:
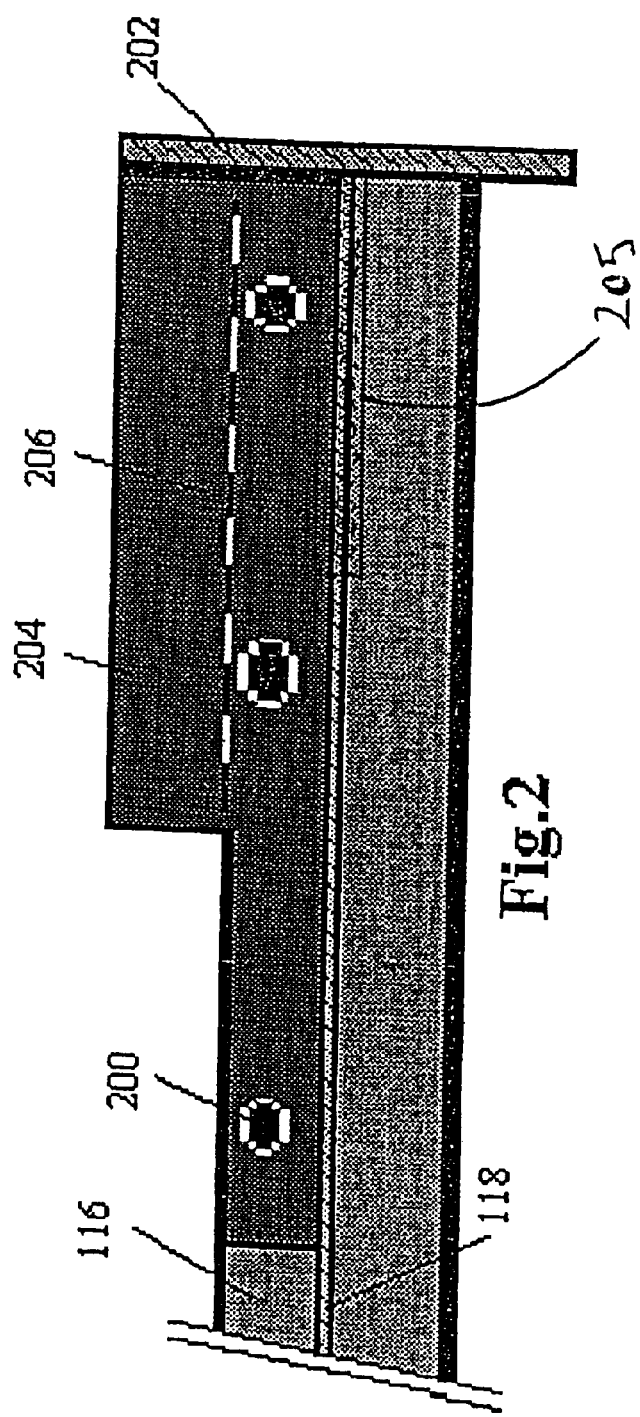
FIG. 2 is a partially schematic cross section view of the preferred embodiment of FIG. 1 showing the proximal portion of the device plunger.

The plunger 116 partially pictured in FIG. 1 and with the remainder shown in FIG. 2. The plunger is constructed such that it resembles four vanes (118) joined at their axis and terminating at the distal end in a means to attach the plunger tip (110). Such means is common in the industry and may be either a threaded screw type attachment (as shown) or a barb over which the plunger tip (110) is placed and is thus secured. The proximal end of the vanes terminates in a plunger thumb plate (202) as shown in FIG. 2. FIG. 2

The plunger (116), the plunger vanes (118) as well as the plunger thumb plate (202), as well as the flag stop (204) and the flag attachment points (200) are shown in FIG. 2. The flag stop (204) is attached to a vane (118) of the plunger (116) to effect an interruption in the process of depressing of the plunger (116) and thereby stop the fluids (122, 124) from being ejected from the syringe. In order for the plunger (116) to be pressed further into the syringe (106), the flag stop (204) must be snapped off at the perforations (206) after which the plunger may be depressed further into the syringe (106).

The purpose of such an interruption caused by the flag stop (204) is to enable the signaling of a sequenced event that should be accomplished before the remainder of the fluids (122, 124) in the syringe are dispensed. This could be simply waiting some period of time prior to dispensing a hardener, for example.

It should be noted that there are also many ways to accomplish the flag stop function other than that illustrated. A simple pin and hole variation, for example, may also be used. Clips aligned with slots in the plunger vanes (118) would also be suitable. It is further noted that multiple such flags may be used in a single application in accordance with the principles of the present invention. For instance, a second flag stop (205) is attached to vane (118). As is shown in FIG. 2, the second flat stop (205) is perpendicular to the plane of the drawing and likewise perpendicular to the first flat stop (204) and oriented rearward of the first stop in the direction of travel of the plunger.

FIG. 3 through FIG. 6 illustrate the use of the flag stop (204). In FIG. 3, the syringe is shown just prior to being used. The flag stop (204) is intact and positioned to allow about half of the fluid (122) in the distal chamber to be dispensed. FIG. 4 illustrates this preferred embodiment of the device after the distal puncture diaphragm (108) has been pierced by the distal end cap slotted spike (104) allowing a portion of the fluid (122) in the distal fluid chamber to be dispensed. This process was halted by the flag stop (204) when forward motion of the plunger (116) caused the flag stop (204) to meet the proximal finger grip (114) at its proximal surface. An application where this would be practical exists when in the medical industry it is necessary to "flood" a catheter extension that would be attached to the distal end cap's (100) end cap termination (102). The flooding is necessary to avoid infusion of air into the patients catheter. After the flooding is completed, the device is connected to the patient's catheter and the flag stop (204) is removed and further motion of the plunger (116) is enabled.

Notably, the plunger may be drawn back without interference. This is important when used in a medical application such as an infusion process. It is through the drawing back that the patency of a catheter is usually ascertained. The process is such that the device is connected and a small amount of fluid is infused and then the plunger is drawn back to allow blood to be seen either exiting the patients catheter or entering the catheter extension. This assures a properly placed catheter that remains patent to the blood vessel indeed exists.

FIG. 5 shows the flag stop (204) with a portion of the flag stop (204) having been removed by snapping it off at the provided perforations (206). The portion of the flag stop that remains may have additional stops that would work to also affect a stop.

FIG. 6 shows the plunger (116) advanced to the point where the second puncture diaphragm (108) has been impaled upon the slotted spike (104) and the fluid (124) in the proximal fluid chamber may now be dispensed from the device. Shown also in FIG. 6 are additional items that might be used in a medical application.

Such additional items comprise a means to connect to the syringe end cap termination (102) which in this case is a female luer lock (600) and a short 5–6 inch length of small bore tubing (602) which terminates, at its distal end, in an adapter (604). The adapter (604) consists of a male luer slip (608) and its protective cover (610) and a wipeable septum (606).

FIG. 6, which illustrates a preferred embodiment of the invention, includes the female luer lock (600) the small bore tubing (602), and the adapter (604) with its wipeable septum (606), male luer lock (608) with protective cover (610). It is noted that FIGS. 3, 4, 5, and 6 represent the same syringe device and application although the items above with 600 series numbers are only shown once in FIG. 6.

In the preferred embodiment of a medical device, the distal fluid (122) is saline and the proximal fluid (124) is Heparin. The volumes of each are 10 ml and 5 ml respectively whereby the syringe is sized at approximately 50 ml total volume to allow for device component space. The device being prefilled with these fluids is appropriately packaged and labeled according to current medical device manufacture as shown in FIG. 3 (with the additional 600 series numbered items shown in FIG. 6).

Such a device would be suitable for application in a catheter flushing operation in preparation for the application of prescribed active medication followed by the application of an anticoagulant. The steps in this process are as follows. The operator unwraps the device and removes protective cap (610). The operator presses the plunger (116) until the distal rupture diaphragm (108) is punctured by the slotted spike (104) allowing the saline (distal fluid (122)) to flood the attached small bore tubing (602) and exit the adapter (604) via the male luer (608). This removes any air present and replaces it with saline. The operator then connects the male luer (608) to the patient's catheter (not shown). The operator may now draw back on the syringe to visually witness blood being removed from the patient. This is done to assure that the patient's catheter is patent and without blockage. The operator may, if all is in order, proceed to press the plunger (116) further to administer saline (122) to the patient's catheter site. This will flush away any anticoagulants from the catheter site. The operator will be interrupted by the flag stop (204) as it makes contact with the proximal finger grips (114). There would be a notation on the flag stop (204) that instructs the operator to administer the medication before removing the flag stop (204).

Then the operator would insert the needle of a separate syringe, containing the active medication, into the wipeable septum (606) after first wiping the wipeable septum (606) with an alcohol swab followed by a drying gauze wipe. An alternative to this, should the active medication be an IV drip circumstance, would be to remove the Male luer (608) and for it substitute the IV drip until done. The male lure (608) would be hygienically capped until the active medication were finished and removed, and then the male luer (608) would be replaced in the patients catheter. Normally this would not be done and a needle would be added to the IV drip and inserted into the septum. All of these options are offered in the arrangement described. Once the operator has administered the active medication, which may take a few seconds or an extended period of hours, the operator returns to the device and is reminded by the notation on the flag stop (204) that the flag stop should be disabled by removing the flag by means of the perforations (206) provided. It is noted that at this time that only approximately half (5 ml) of the saline fluid (122) has been administered up to this point. Once the operator ace has removed the flag, the plunger may be smoothly moved forward to finish dispensing the remaining 5 ml of saline and continue on to puncture the second puncture diaphragm (108) and thereafter administer the Heparin fluid (124) in its 5 ml entirety. This step, in one uninterrupted motion, has isolated the active medication, by use of saline (122), from the anticoagulant Heparin. The Heparin remains in the patient's catheter to prevent clotting. The operator removes the device from the patient's catheter and places a sterile cap on that patient catheter. The device, having been exhausted of fluids is disposed of as medical waste.

The foregoing specific embodiments of the present invention as set forth in the specification herein are for illustrative purposes only. Various changes and modifications may be made within the spirit and scope of this invention.

What is claimed is:

1. A syringe apparatus comprising:

a tubular body;

a tubular cartridge capable of containing fluid mounted in said body, said tubular cartridge being sealed at one end by a distal diaphragm and further sealed upstream with a proximal diaphragm, an area between the distal and proximal diaphragms defining a space for holding a distal fluid, said distal diaphragm having a central area of thinner cross-section than an adjacent area of the distal diaphragm;

a hollow tubular spike mounted at one end of said body and facing inwardly into said tubular body;

a plunger mounted within said tubular body for moving said cartridge towards said spike whereby said spike is operative to puncture said central area of said distal diaphragm and thereby allow said fluid to flow from said cartridge through the hollow of said spike out of said tubular body, the plunger having a plurality of vanes, and another area between the proximal diaphragm and plunger defining a space for holding a proximal fluid, said spike being operative to puncture said proximal diaphragm and fluid to flow from said cartridge through the hollow of said spike out of said tubular body; and a means for effecting an interruption in moving the plunger towards the spike and thereby controlling fluid quantity flowing from the cartridge through the spike, the means being removably attached in a perforated manner to a vane of the plunger and projecting outwardly from the tubular body, the means comprising a first flag stop attached to one of said plurality of vanes and a second flag stop attached to another of said plurality of vanes rearwardly of said first flag stop in a direction of travel of said plug.

2. A syringe apparatus according to claim 1 wherein the proximal diaphragm has a central area of thinner cross-section than an adjacent area of the proximal diaphragm.

3. A syringe apparatus according to claim 1 wherein the distal diaphragm has a U-shaped recess formed by the central and adjacent areas.

* * * * *